United States Patent
Arnin (10) Patent No.: US 8,968,406 B2
(45) Date of Patent: Mar. 3, 2015

(54) SPINAL IMPLANT HAVING A POST-OPERATIVE ADJUSTABLE DIMENSION

(75) Inventor: Uri Arnin, Kiryat Tivon (IL)

(73) Assignee: Spine21 Ltd., Haifa (IL)

(*) Notice: Subject to any disclaimer, the term of this patent is extended or adjusted under 35 U.S.C. 154(b) by 560 days.

(21) Appl. No.: 12/741,031

(22) PCT Filed: Oct. 29, 2008

(86) PCT No.: PCT/IL2008/001423
§ 371 (c)(1),
(2), (4) Date: May 2, 2010

(87) PCT Pub. No.: WO2009/060427
PCT Pub. Date: May 14, 2009

(65) Prior Publication Data
US 2010/0262247 A1    Oct. 14, 2010

Related U.S. Application Data

(63) Continuation of application No. 11/937,019, filed on Nov. 8, 2007, now Pat. No. 8,241,331.

(51) Int. Cl.
*A61F 2/44* (2006.01)
*A61B 17/02* (2006.01)
(Continued)

(52) U.S. Cl.
CPC ............ *A61F 2/441* (2013.01); *A61B 17/025* (2013.01); *A61B 17/70* (2013.01); *A61B 17/7014* (2013.01); *A61B 17/7016* (2013.01); *A61B 17/7017* (2013.01); *A61B 17/7062* (2013.01); *A61F 2/4455* (2013.01); *A61B 2017/00022* (2013.01); *A61B 2017/00212* (2013.01); *A61B 2017/00221* (2013.01); *A61B 2017/00539* (2013.01); *A61B 2017/00544* (2013.01); *A61B 2017/00557* (2013.01);
(Continued)

(58) Field of Classification Search
CPC ............ A61F 2002/30523; A61F 2002/30525; A61F 2002/30527; A61F 2002/30518; A61F 2002/3052; A61F 2002/30522; A61F 2002/3055; A61F 2002/30556; A61F 2002/30601; A61F 2002/30411; A61F 2002/30553; A61F 2002/30579; A61F 2220/0025
USPC ............... 623/17.11–17.16; 606/247–249, 90
See application file for complete search history.

(56) References Cited

U.S. PATENT DOCUMENTS 2,333,033 A * 10/1943 Mraz ............................... 606/57
4,548,199 A * 10/1985 Agee ............................... 606/57
(Continued)

FOREIGN PATENT DOCUMENTS

| DE | 19856013 | 6/2000 |
|---|---|---|
| WO | 2006034013 A1 | 3/2006 |
| WO | 2006065419 A2 | 6/2006 |

*Primary Examiner* — Mary Hoffman
(74) *Attorney, Agent, or Firm* — Daniel J. Swirsky; AlphaPatent Associates Ltd.

(57) ABSTRACT

A spinal implant (40) including first spinal attachment member (44) for attaching to a first spinal portion (41), second spinal attachment member (46) for attaching to a second spinal portion (42), and a post-implantation variable dimension device disposed between the first and second spinal attachment members, which is operable after completing surgery in which said spinal implant was installed into a patient, to cause relative movement between the first and second spinal attachment members.

10 Claims, 9 Drawing Sheets

(51) Int. Cl.
*A61B 17/70* (2006.01)
*A61B 17/00* (2006.01)
*A61F 2/30* (2006.01)
*A61F 2/48* (2006.01)

(52) U.S. Cl.
CPC .............. *A61B 2017/00734* (2013.01); *A61B 2017/0256* (2013.01); *A61F 2002/30471* (2013.01); *A61F 2002/30507* (2013.01); *A61F 2002/30525* (2013.01); *A61F 2002/30527* (2013.01); *A61F 2002/3055* (2013.01); *A61F 2002/30553* (2013.01); *A61F 2002/30556* (2013.01); *A61F 2002/30601* (2013.01); *A61F 2002/30668* (2013.01); *A61F 2002/482* (2013.01); *A61F 2002/485* (2013.01); *A61F 2220/0025* (2013.01); *A61F 2220/0091* (2013.01); *A61F 2250/0001* (2013.01); *A61F 2250/0008* (2013.01); *A61F 2250/0009* (2013.01)
USPC ..................................... 623/17.16

(56) References Cited

U.S. PATENT DOCUMENTS

| | | | | |
|---|---|---|---|---|
| 4,573,459 | A * | 3/1986 | Litton | 606/58 |
| 4,599,086 | A * | 7/1986 | Doty | 606/86 A |
| 4,636,217 | A * | 1/1987 | Ogilvie et al. | 623/17.11 |
| 4,747,394 | A * | 5/1988 | Watanabe | 600/232 |
| 4,827,918 | A * | 5/1989 | Olerud | 606/258 |
| 4,929,247 | A * | 5/1990 | Rayhack | 606/53 |
| 4,931,055 | A * | 6/1990 | Bumpus et al. | 606/60 |
| 5,097,820 | A * | 3/1992 | Shulman et al. | 600/237 |
| 5,147,358 | A * | 9/1992 | Remmler | 606/57 |
| 5,364,396 | A * | 11/1994 | Robinson et al. | 606/53 |
| 5,405,391 | A * | 4/1995 | Hednerson et al. | 623/17.15 |
| 5,413,602 | A * | 5/1995 | Metz-Stavenhagen | 623/17.15 |
| 5,437,668 | A * | 8/1995 | Aronson et al. | 606/57 |
| 5,458,641 | A * | 10/1995 | Ramirez Jimenez | 623/17.11 |
| 5,514,180 | A * | 5/1996 | Heggeness et al. | 623/17.16 |
| 5,601,551 | A * | 2/1997 | Taylor et al. | 606/54 |
| 5,616,117 | A * | 4/1997 | Dinkler et al. | 600/232 |
| 5,895,387 | A * | 4/1999 | Guerrero et al. | 606/71 |
| 5,976,125 | A * | 11/1999 | Graham | 606/32 |
| 6,007,535 | A * | 12/1999 | Rayhack et al. | 606/57 |
| 6,126,660 | A * | 10/2000 | Dietz | 606/90 |
| 6,245,075 | B1 * | 6/2001 | Betz et al. | 606/105 |
| 6,358,255 | B1 * | 3/2002 | Testa | 606/105 |
| 6,413,231 | B1 * | 7/2002 | Berman et al. | 601/38 |
| 6,454,806 | B1 * | 9/2002 | Cohen et al. | 623/17.15 |
| 6,508,817 | B1 * | 1/2003 | Pensler et al. | 606/57 |
| 6,616,672 | B1 * | 9/2003 | Essiger | 606/105 |
| 7,011,658 | B2 * | 3/2006 | Young | 606/258 |
| 7,018,415 | B1 * | 3/2006 | McKay | 623/17.15 |
| 7,029,472 | B1 * | 4/2006 | Fortin | 606/60 |
| 7,083,650 | B2 * | 8/2006 | Moskowitz et al. | 623/17.11 |
| 7,531,002 | B2 * | 5/2009 | Sutton et al. | 623/17.15 |
| 7,601,156 | B2 * | 10/2009 | Robinson | 606/90 |
| 7,736,356 | B2 * | 6/2010 | Cooper et al. | 606/1 |
| 2003/0144669 | A1 * | 7/2003 | Robinson | 606/90 |
| 2004/0030395 | A1 * | 2/2004 | Blunn et al. | 623/18.12 |
| 2004/0088054 | A1 * | 5/2004 | Berry | 623/17.11 |
| 2004/0097938 | A1 * | 5/2004 | Alleyne | 606/69 |
| 2005/0004573 | A1 * | 1/2005 | Abdou | 606/61 |
| 2005/0049590 | A1 * | 3/2005 | Alleyne et al. | 606/61 |
| 2005/0096088 | A1 * | 5/2005 | Bae | 455/558 |
| 2005/0096674 | A1 * | 5/2005 | Loshakove et al. | 606/153 |
| 2005/0165407 | A1 * | 7/2005 | Diaz | 606/90 |
| 2005/0203534 | A1 * | 9/2005 | Mommaerts | 606/90 |
| 2005/0216017 | A1 * | 9/2005 | Fielding et al. | 606/74 |
| 2005/0234555 | A1 * | 10/2005 | Sutton et al. | 623/17.15 |
| 2005/0240182 | A1 * | 10/2005 | Zucherman et al. | 606/61 |
| 2005/0256576 | A1 * | 11/2005 | Moskowitz et al. | 623/17.12 |
| 2006/0004447 | A1 | 1/2006 | Mastrorio et al. | |
| 2006/0058790 | A1 | 3/2006 | Carl | |
| 2006/0085074 | A1 | 4/2006 | Raiszadeh | |
| 2006/0149385 | A1 * | 7/2006 | McKay | 623/17.15 |
| 2007/0162000 | A1 * | 7/2007 | Perkins | 606/61 |
| 2007/0173832 | A1 | 7/2007 | Tebbe | |
| 2007/0198089 | A1 * | 8/2007 | Moskowitz et al. | 623/17.11 |
| 2008/0021466 | A1 * | 1/2008 | Shadduck et al. | 606/61 |
| 2008/0027550 | A1 * | 1/2008 | Link et al. | 623/17.16 |
| 2009/0081602 | A1 * | 3/2009 | Ayan | 433/7 |
| 2009/0093820 | A1 * | 4/2009 | Trieu et al. | 606/103 |
| 2009/0093890 | A1 * | 4/2009 | Gelbart | 623/24 |
| 2009/0125062 | A1 * | 5/2009 | Arnin | 606/246 |
| 2009/0259107 | A1 * | 10/2009 | Crenshaw et al. | 600/202 |
| 2010/0094306 | A1 * | 4/2010 | Chang et al. | 606/90 |
| 2010/0114103 | A1 * | 5/2010 | Harrison et al. | 606/90 |
| 2011/0172716 | A1 * | 7/2011 | Glerum | 606/279 |
| 2011/0178600 | A1 * | 7/2011 | Moskowitz et al. | 623/17.16 |
| 2012/0041562 | A1 * | 2/2012 | Shachar et al. | 623/17.16 |

* cited by examiner

SPINAL IMPLANT HAVING A POST-OPERATIVE ADJUSTABLE DIMENSION

CROSS-REFERENCE TO RELATED APPLICATIONS

This application is a U.S. National Phase Application under 35 U.S.C. 371 of PCT International Application No. PCT/IL2008/001423, which has an international filing date of Oct. 29, 2008, and which is a continuation of, and claims priority benefit from, U.S. patent application Ser. No. 11/937,019 now U.S. Pat. No. 8,241,331, filed Nov. 8, 2007, and incorporated herein by reference in its entirety.

FIELD OF THE INVENTION

The present invention relates generally to spinal implants and prostheses, and particularly to a spinal implant having a post-operative adjustable dimension.

BACKGROUND OF THE INVENTION

Spinal stenosis, as well as spondylosis, spondylolisthesis, osteoarthritis, scoliosis and other degenerative phenomena may be the cause of back pain, and may be caused by a narrowing of the spinal canal or foramina that result in stress acting on the spinal cord and/or nerve roots.

One of the methods for resolving back pain involves decompression, the removal of bony elements causing the pain, and fusion of two or more adjacent vertebrae. Unfortunately, fusion tends to have significant shortcoming and may cause the problem to migrate to adjacent vertebral components. Among the non-fusion solutions are disc replacement, dynamic stabilization systems and inter-spinous process implants.

Spinal implants with the capability of height adjustment are known. For example, U.S. Pat. Nos. 6,045,579, 6,080,193 and 6,576,016 to Hochshuler et at (issued Apr. 4, 2000, Jun. 27, 2000 and Jun. 10, 2003, respectively) describe an adjustable height fusion device for promoting a spinal fusion between neighboring vertebrae. The device is located within the intervertebral disc space and includes a pair of engaging plates for contacting the vertebrae. An alignment device is used to alter the vertical distance between the engaging plates to customize the apparatus to fit a given patient. In one embodiment, the alignment device includes a pair of struts having a predetermined height and extending between the engaging plates from an anterior end to a posterior end of the apparatus. In another embodiment, the alignment device includes a rotatable connector and cam pins for adjusting the distance between the engaging plates. The alignment device is preferably adapted to vary the distance between the engaging plates such that the height of the apparatus proximate the anterior end is greater than that proximate the posterior end whereby the natural lordosis of the spine is maintained after the apparatus is installed.

However, these prior art devices must be adjusted prior to or during the installation and are not capable of post-operative adjustment.

SUMMARY OF THE INVENTION

The present invention seeks to provide an improved spinal implant (or prosthesis, the terms being used interchangeably) having a post-operative adjustable dimension, such as an inter-spinous process spinal implant, as described in more detail further below.

In one embodiment, at least one of its dimensions of the spinal implant can be modified post-implantation by means of remote control or a mechanical feature that can be connected to an adjustable portion of the implant, such as via a small puncture in the soft tissues. In one example, the adjustable portion (also referred to as a variable dimension mechanism) can have a piston-like configuration hydraulically or pneumatically activated by a small pressure tube. Other mechanical devices may be used and deployed, such as but not limited to, by a shaft, cable or other mechanical features. In another example, the adjustable portion can be electrically powered, such as by an electric motor (powered by electric cord, battery or remote induction), and controlled via remote control.

The prosthesis is configured to bridge between two vertebrae, most preferably but not limited to, adjacent vertebrae. The prosthesis includes a plurality of attachment members (end features) configured to be attached to a plurality of bone attachment points, such as but not limited to, spinous process, vertebral end plates or pedicles (via pedicle screws).

There is thus provided in accordance with a non-limiting embodiment of the present invention a spinal implant including first spinal attachment member for attaching to a first spinal portion, second spinal attachment member for attaching to a second spinal portion, and a post-implantation variable dimension device disposed between the first and second spinal attachment members, which is operable after completing surgery in which said spinal implant was installed into a patient, to cause relative movement between the first and second spinal attachment members.

In accordance with an embodiment of the present invention the first and second spinal attachment members include pedicle screws.

In accordance with an embodiment of the present invention the post-implantation variable dimension device changes a distance between the first and second spinal attachment members.

In accordance with an embodiment of the present invention the post-implantation variable dimension device changes a location of the first and second spinal attachment members both in vertical and sagittal planes.

In accordance with an embodiment of the present invention the first and second spinal attachment members include first and second support plates fitted with threaded shafts which are turned by a gear train, wherein rotation of the gear train changes a distance between the first and second support plates.

In accordance with an embodiment of the present invention the first and second spinal attachment members include first and second support plates inclined with respect to each other.

In accordance with an embodiment of the present invention the post-implantation variable dimension device is hydraulically or pneumatically operated.

In accordance with an embodiment of the present invention the post-implantation variable dimension device includes hinged arms which are pivotally connected to and moved by a screw mechanism.

In accordance with an embodiment of the present invention the post-implantation variable dimension device is electrically operated.

In accordance with an embodiment of the present invention the post-implantation variable dimension device includes an internal, implanted portion. The internal portion may include at least one of an electrical piston, an electric motor, a microprocessor, an RF emitter/transmitter, an LVDT, a strain sensor, an electric coil, a battery, and a capacitor.

In accordance with an embodiment of the present invention the post-implantation variable dimension device includes an external control portion. The external control portion may include at least one of a control panel, a processor, an RF transmitter/emitter, a magnetic power source, an electric coil and a cellular communication device. The communication between the external control portion and the implanted portion may be controlled by a code or password to protect against undesired operation of the internal device.

In accordance with an embodiment of the present invention the post-implantation variable dimension device is inflatable.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
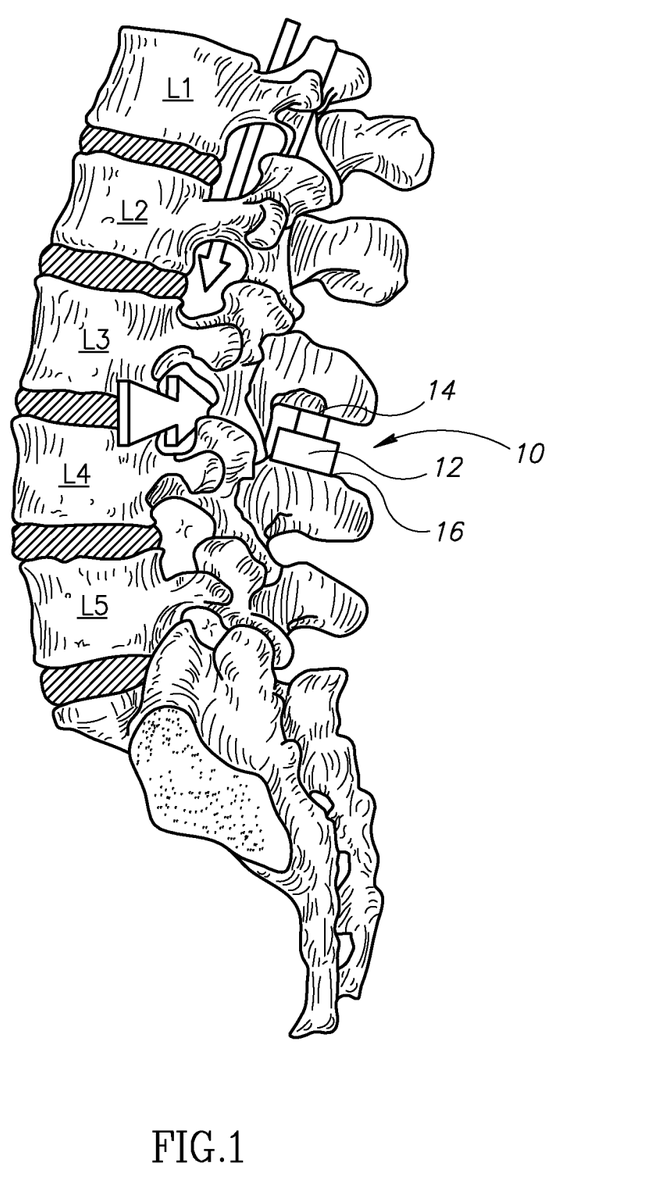
FIG. 1 is a simplified pictorial illustration of a spinal implant including a post-implantation variable dimension device, constructed and operative in accordance with an embodiment of the invention, implanted between two adjacent spinous processes.

Reference is now made to FIG. 1, which illustrates a spinal implant 10, constructed and operative in accordance with an embodiment of the invention.

Spinal implant 10 is shown implanted between two adjacent spinous processes of the lumbar spine (in this example, spinal implant 10 is an interspinous process device). Spinal implant 10 includes a post-implantation variable dimension device 12 disposed between a first (upper) support end plate (spinal attachment member) 14 and a second (lower) support end plate (spinal attachment member) 16. The post-implantation variable dimension device 12 may include a post arranged for linear motion (slightly tilted from vertical in the sense of the drawing), such as by means of a miniature linear actuator which is remote controlled. In general, post-implantation variable dimension device 12 may be constructed in accordance with any of the embodiments described below with reference to FIGS. 6-9.

Figure 2:
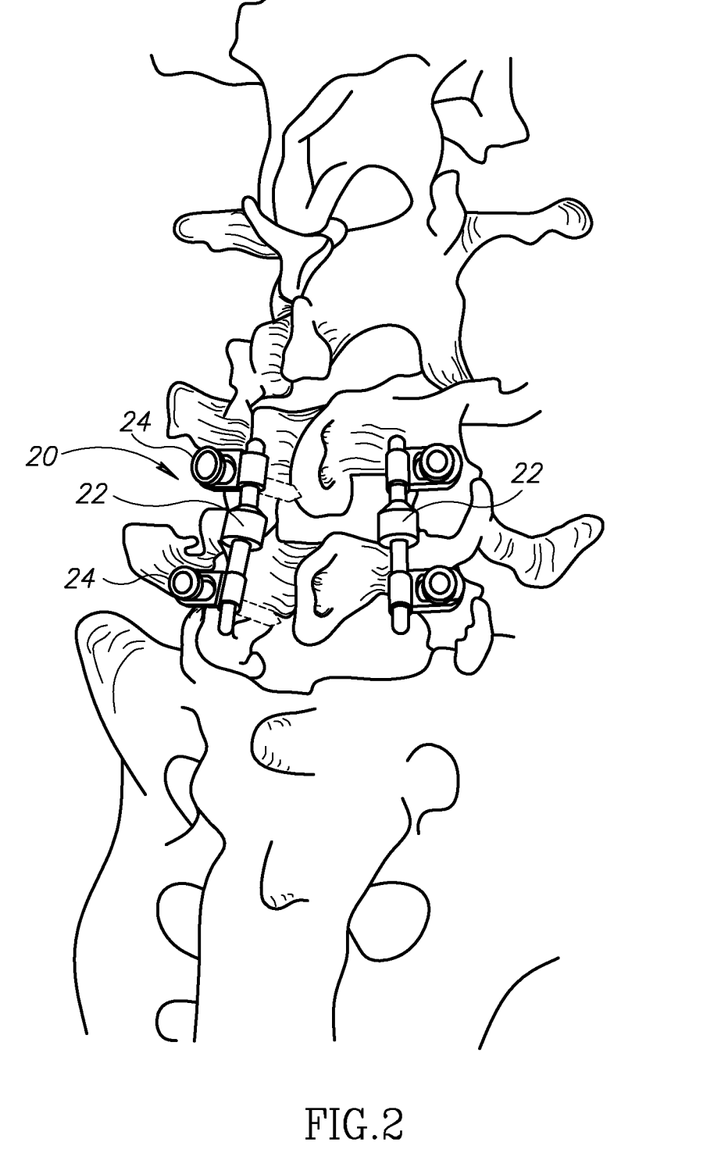
FIG. 2 is a simplified pictorial illustration of a spinal implant including a post-implantation variable dimension device, constructed and operative in accordance with another embodiment of the invention, connected to pedicle screws so that actuating the variable dimension mechanism can change the distance between the screws.

Reference is now made to FIG. 2, which illustrates a spinal implant 20, constructed and operative in accordance with another embodiment of the invention. Spinal implant 20 includes a post-implantation variable dimension device 22, and is connected to pedicle screws 24 (spinal attachment members 24). Actuation of variable dimension device 22 changes the distance between screws 24. Here too, post-implantation variable dimension device 22 may include a post arranged for linear motion, such as by means of a miniature linear actuator which is remote controlled. In general, post-implantation variable dimension device 22 may be constructed in accordance with any of the embodiments described below with reference to FIGS. 6-9.

Figure 3:
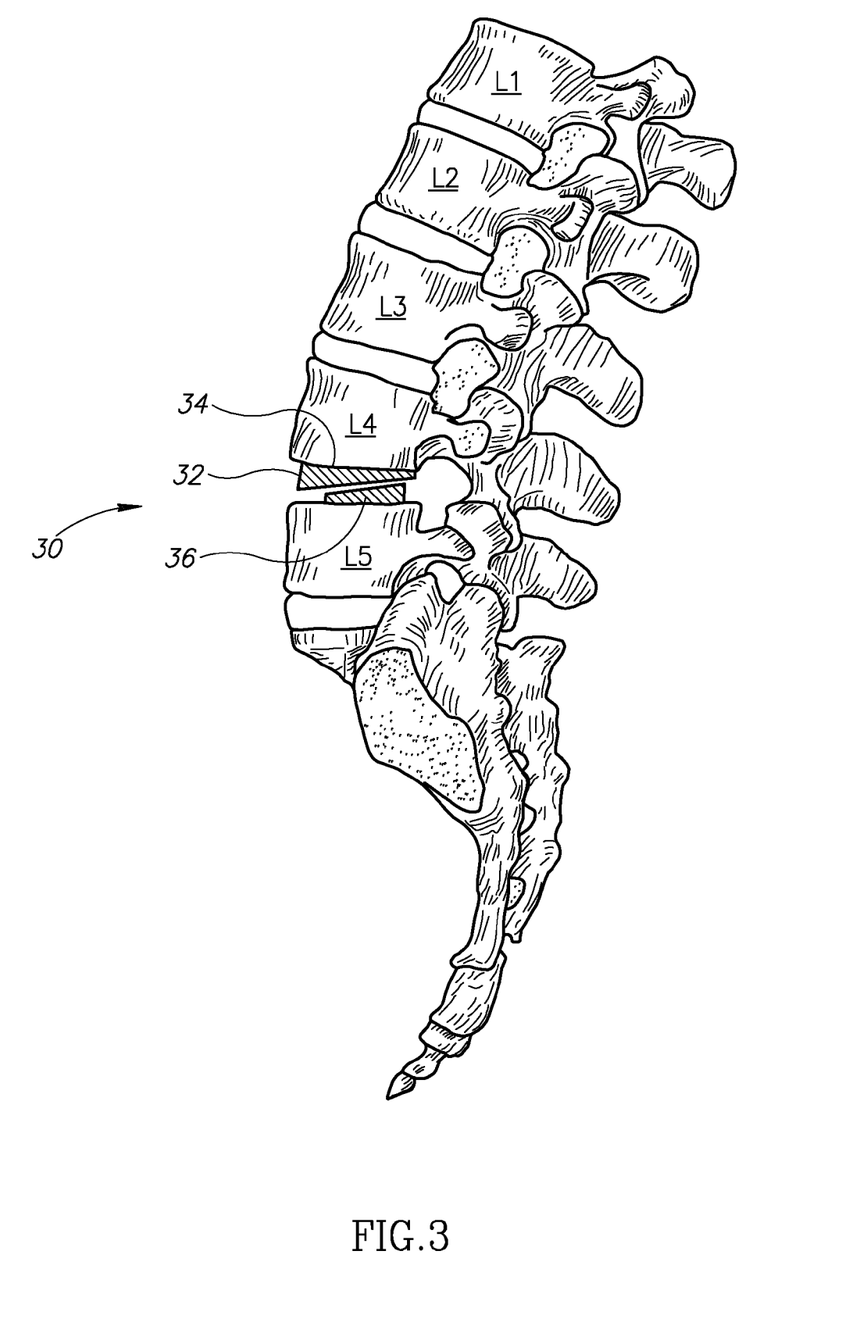
FIG. 3 is a simplified pictorial illustration of a spinal implant including a post-implantation variable dimension device, constructed and operative in accordance with yet another embodiment of the invention, inserted in between two adjacent vertebrae.

Reference is now made to FIG. 3, which illustrates a spinal implant 30 including a post-implantation variable dimension device 32, constructed and operative in accordance with yet another embodiment of the invention, inserted in between two adjacent vertebrae (e.g., L4 and L5). Spinal implant 30 includes a first (upper) support plate 34 connected to and supporting an upper vertebra, and a second (lower) support plate 36 connected to and supporting a lower vertebra. The variable dimension device 32 is installed between first and second support plates (spinal attachment members) 34 and 36. Actuation of variable dimension device 32 changes the distance between first and second support plates 34 and 36, and can change the location between the two adjacent vertebrae both in the vertical and the sagittal planes. The post-implantation variable dimension device 32 may be constructed in accordance with the embodiment described below with reference to FIG. 5.

Figure 4:
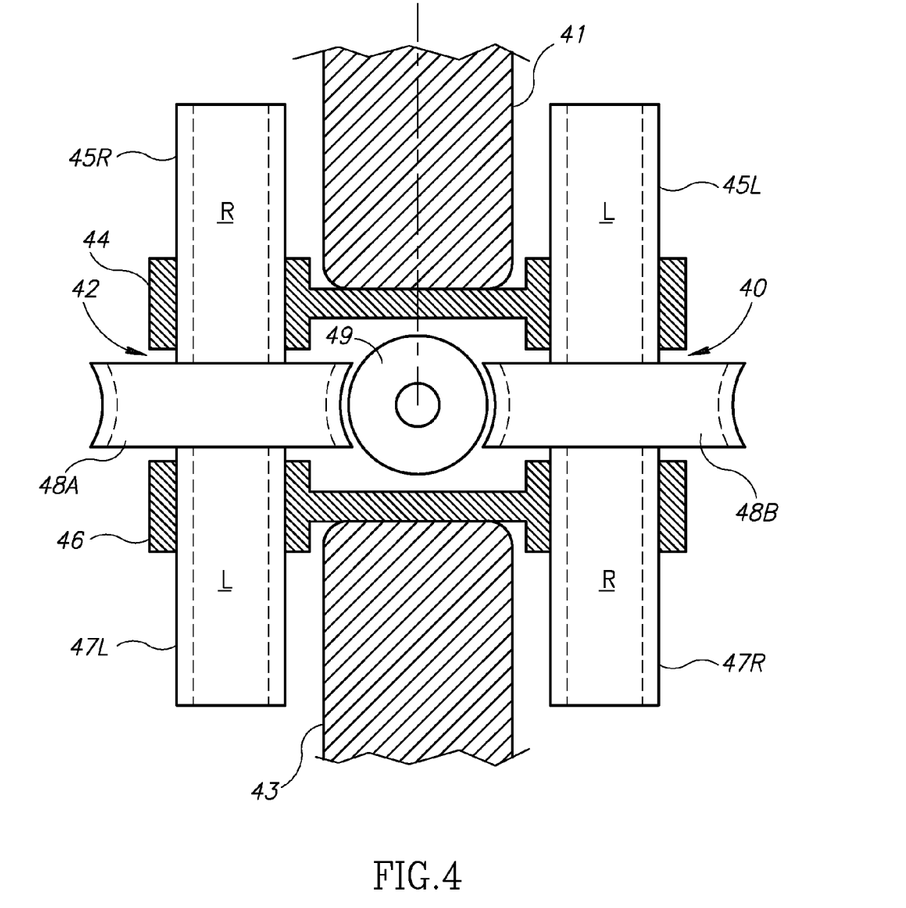
FIG. 4 is a simplified pictorial illustration of a spinal implant including a post-implantation variable dimension device, constructed and operative in accordance with still another embodiment of the invention, used to create an optimal distraction between two adjacent spinous processes.

Reference is now made to FIG. 4, which illustrates a spinal implant 40 including a post-implantation variable dimension device 42, constructed and operative in accordance with still another embodiment of the invention. Implant 40 can be used to create an optimal distraction between two adjacent spinous processes, such as the superior spinous process 41 and inferior spinous process 43.

Spinal implant 40 includes first and second support plates (spinal attachment member) 44 and 46 that respectively support the superior spinous process 41 and inferior spinous process 43. First and second support plates 44 and 46 are each tapped with threaded holes to accept threaded shafts 45L and 45R, and 47L and 47R, respectively. Threaded shafts 45L and 47L have left-handed threads, while threaded shafts 45R and 47R have right-handed threads.

Gear pulleys 48A and 48B are connected to threaded shafts 45L, 45R, 47L and 47R, and are driven by a worm gear 49. Rotation of worm gear 49 changes the distance between first and second support plates 44 and 46 and the supported spinous processes.

Figure 5:
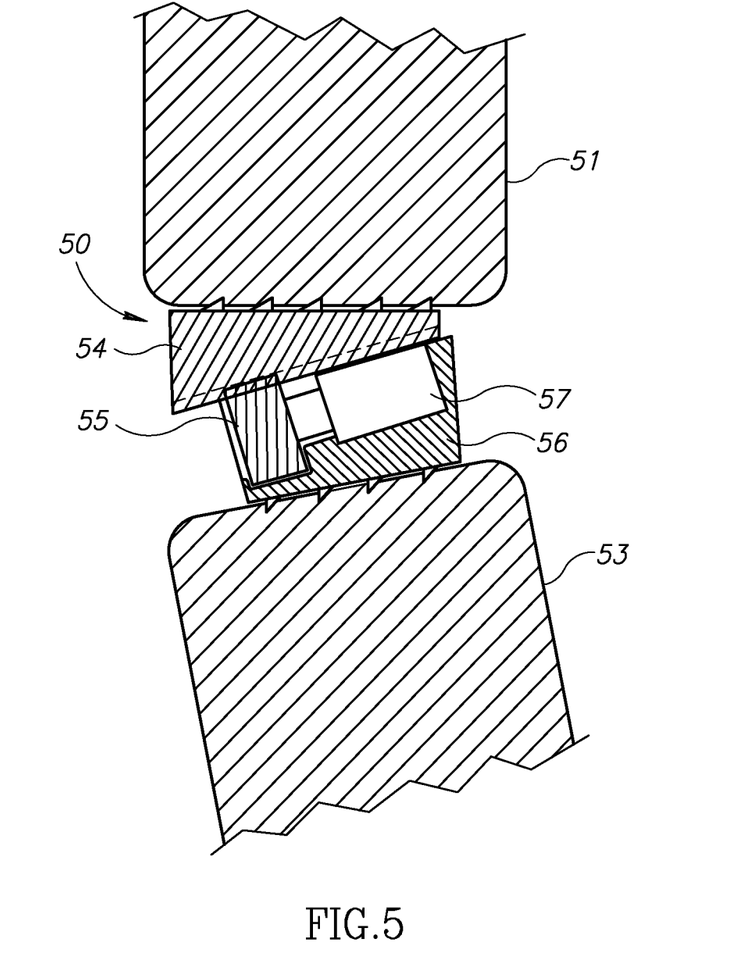
FIG. 5 is a simplified pictorial illustration of a spinal implant including a post-implantation variable dimension device, constructed and operative in accordance with yet another embodiment of the invention, used to change the location of adjacent vertebrae.

Reference is now made to FIG. 5, which illustrates a spinal implant 50 including a post-implantation variable dimension device 52, constructed and operative in accordance with yet another embodiment of the invention.

Spinal implant 50 may be used to change the location of adjacent vertebrae 51 and 53. Spinal implant 50 includes a first (upper) support plate 54 having a threaded slot in which a threaded screw 55 is threadedly received. Spinal implant 50 includes a second (lower) support plate 56 that includes a recess in which an electrical motor (or actuator) 57 is mounted. The electrical motor 57 (which may be remote controlled) turns screw 55, which causes first support plate 54 to slide with respect to second support plate 56. The inclined mating between first and second support plates (spinal attachment members) 54 and 56 causes a change in the adjacent location between the two vertebras, both in the vertical and the sagittal planes.

Figure 6:
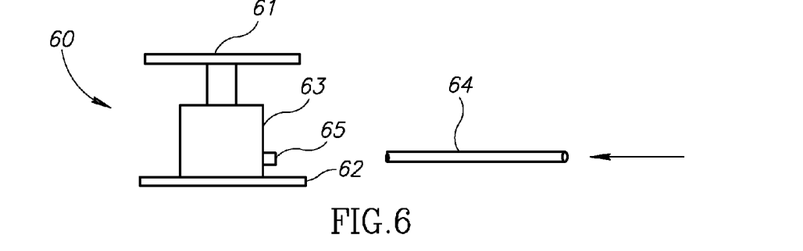
FIG. 6 is a simplified pictorial illustration of a hydraulically or pneumatically operated post-implantation variable dimension device, constructed and operative in accordance with an embodiment of the invention.

Reference is now made to FIG. 6, which illustrates a hydraulically or pneumatically operated post-implantation variable dimension device 60, constructed and operative in accordance with an embodiment of the invention. Variable dimension device 60 includes two end plates (spinal attachment members) 61 and 62, both attached to a piston 63. Piston 63 is fluidly actuated (that is, either hydraulically or pneumatically), such as by means of compressed liquid (e.g., water) or gas (e.g., air). The compressed fluid is introduced to piston 63 by means of a tube 64 which is connected to a fluid inlet 65.

Figure 7:
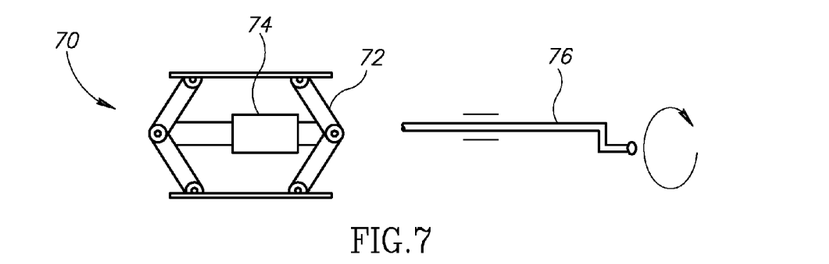
FIG. 7 is a simplified pictorial illustration of a mechanically operated post-implantation variable dimension device, constructed and operative in accordance with an embodiment of the invention.

Reference is now made to FIG. 7, which illustrates a mechanically operated post-implantation variable dimension device 70, constructed and operative in accordance with an embodiment of the invention. Variable dimension device 70 includes hinged arms 72 which are pivotally connected to and moved by a male/female screw mechanism 74 operated by a turn-handle 76.

Figure 8:
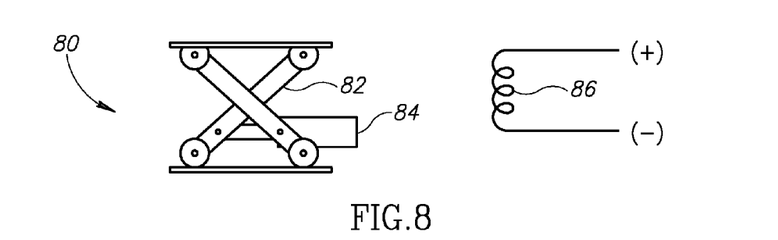
FIG. 8 is a simplified pictorial illustration of an electrically operated post-implantation variable dimension device, constructed and operative in accordance with an embodiment of the invention.

Reference is now made to FIG. 8, which illustrates an electrically operated post-implantation variable dimension device 80, constructed and operative in accordance with an embodiment of the invention. Variable dimension device 80 includes hinged arms 82 which are pivotally connected to and moved by an electrical piston (electrical actuator or solenoid) 84, which may be externally operated by an inductance coil 86.

The electrically operated post-implantation variable dimension device 80 may have an internal, implanted portion and/or an external, control portion. The internal portion may include, without limitation, electrical piston 84, an electric motor, microprocessor, RF emitter/transmitter, LVDT (linear variable differential transducer), strain sensor, electric coil for direct energy transfer into the motor from an external coil, battery, capacitor to accumulate energy, or any combination thereof.

The external portion may include, without limitation, a control panel, processor, RF transmitter/emitter, magnetic power source, electric coil to transfer energy to the internal unit, or any combination thereof. The external portion may also include a cellular communication device to allow remote control by the physician. A code or password may be incorporated into the control system to prevent unwanted operation.

Figure 9:
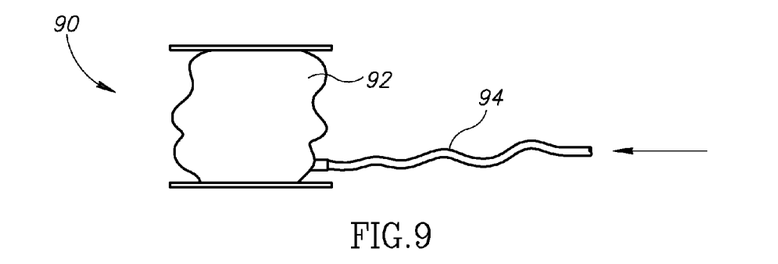
FIG. 9 is a simplified pictorial illustration of an inflatable post-implantation variable dimension device, constructed and operative in accordance with an embodiment of the invention.

Reference is now made to FIG. 9, which illustrates an inflatable post-implantation variable dimension device 90, constructed and operative in accordance with an embodiment of the invention. Variable dimension device 90 includes an inflatable pillow or cushion 92 inflatable via a small tube 94.

Figure 10:
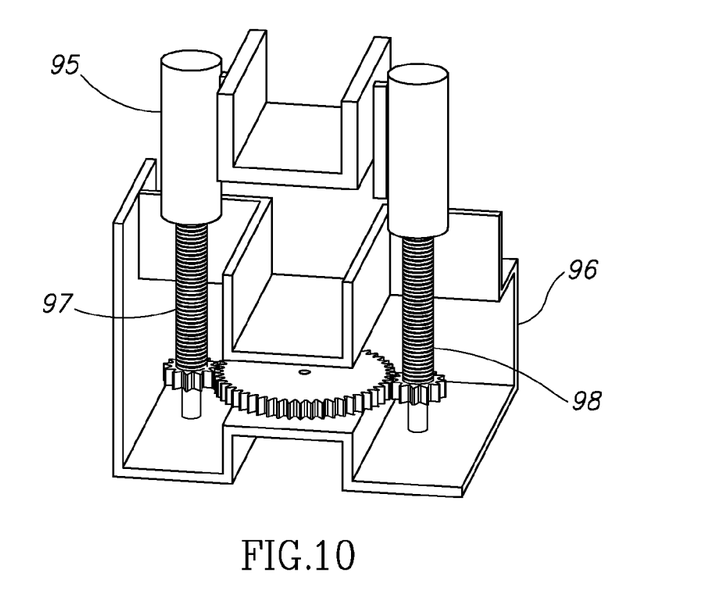
FIG. 10 is a simplified pictorial illustration of a spinal implant including a post-implantation variable dimension device, constructed and operative in accordance with still another embodiment of the invention, used to create an optimal distraction between two adjacent spinous processes using two bilateral, identically threaded lifting screws.

Reference is now made to FIG. 10, which illustrates a post-implantation variable dimension device that can be placed between two adjacent spinous processes, constructed and operative in accordance with an embodiment of the invention. The variable dimension device includes a first supporting element 95 and a second supporting element 96. Two bilateral, identically threaded (same direction of rotation) screws 97 and 98 are used to control the distance between supporting elements 95 and 96.

Figure 11:
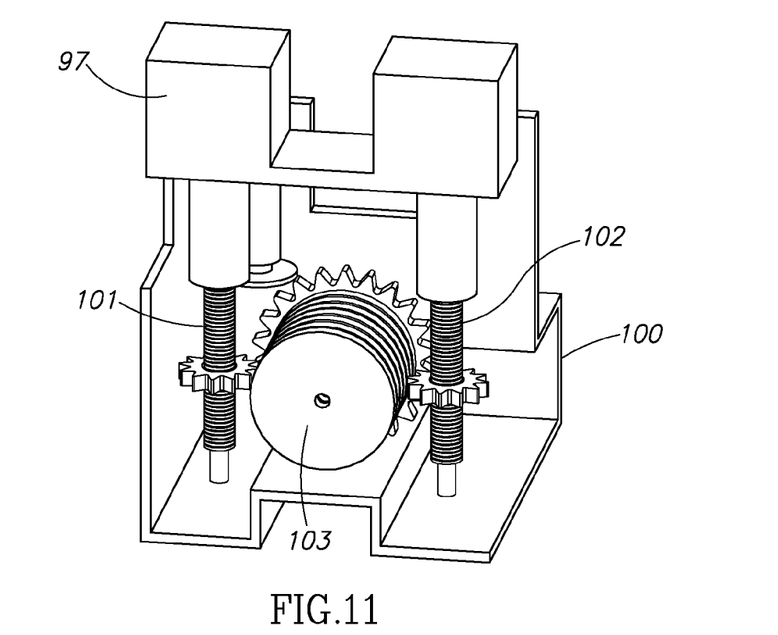
FIG. 11 is a simplified pictorial illustration of a spinal implant including a post-implantation variable dimension device, constructed and operative in accordance with yet another embodiment of the invention, used to create an optimal distraction between two adjacent spinous processes using two bilateral right handed and left handed lifting screws.

Reference is now made to FIG. 11, which illustrates a post-implantation variable dimension device that can be placed between two adjacent spinous processes, constructed and operative in accordance with another embodiment of the invention. This variable dimension device includes a first supporting element 99 and a second supporting element 100. Two bilateral, differently threaded (e.g., right and left handed threads) screws 101 and 102 are used to control the distance between supporting elements 99 and 100. The screws are driven by a worm gear 103. The different threads may be used to better lock the mechanism at any given point.

Figure 12:
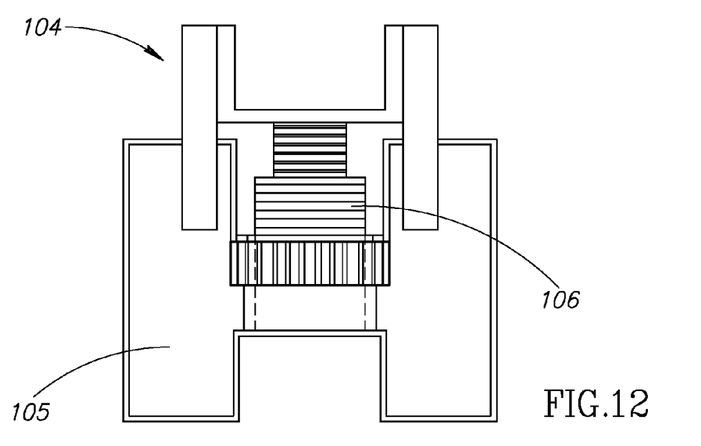
FIG. 12 is a simplified pictorial illustration of a spinal implant including a post-implantation variable dimension device, constructed and operative in accordance with still another embodiment of the invention, used to create an optimal distraction between two adjacent spinous processes using multiple concentric lifting screws.

Reference is now made to FIG. 12, which illustrates a post-implantation variable dimension device that can be placed between two adjacent spinous processes, constructed and operative in accordance with another embodiment of the invention. This variable dimension device includes a first supporting element 104 and a second supporting element 105. Two concentric screws 106 are used to control the distance between supporting elements 104 and 105. By using multiple concentric screws, the mechanism can be rotated a greater distance than with a single central screw.

Figure 13:
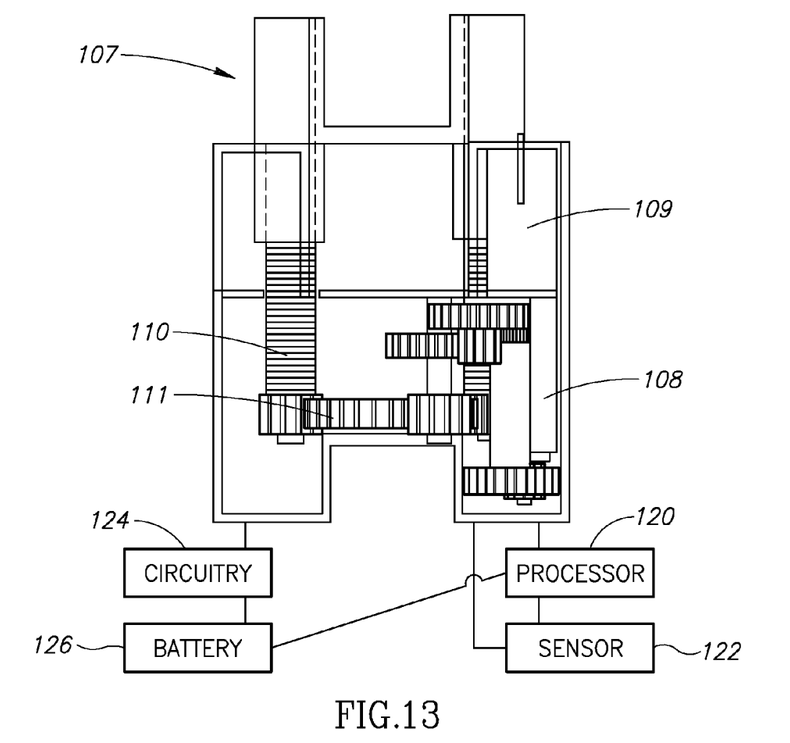
FIG. 13 is a simplified pictorial illustration of a spinal implant including a post-implantation variable dimension device, constructed and operative in accordance with yet another embodiment of the invention, used to create an optimal distraction between two adjacent spinous processes using two bilateral identically threaded lifting screws with electric motor and gear train.

Reference is now made to FIG. 13, which illustrates a post-implantation variable dimension device that can be placed between two adjacent spinous processes, constructed and operative in accordance with another embodiment of the invention. This variable dimension device includes a first supporting element 107 and a second supporting element 108. Two bilateral, identically threaded screws 110 are used to control the distance between supporting elements 107 and 108. The lifting screws are driven by a gear train 111 activated by an electric motor 109.

Thus, in the embodiments of FIGS. 10-13, the spinal implant can be located between two adjacent spinous processes such that the inferior spinous process is supported by a first element of the implant and the superior spinous process is supported by a second element of the implant. The two supporting elements are separated from each other along a generally horizontal plane, and a mechanical or electro-mechanical mechanism can control the distance between the two supporting elements.

Another option of any of the embodiments of the invention is shown in FIG. 13. The spinal implant can include a processor 120 and sensor 122 that control the post-implantation variable dimension device as a function of a load applied on, or a distance between, the first and second spinal attachment members. The post-implantation variable dimension device can be programmable to be activated at any desired time interval for any desired load and travel limits. For conserving power, the post-implantation variable dimension device can include circuitry 124 for operating in a sleep mode. The post-implantation variable dimension device may be powered by a rechargeable battery 126 that is chargeable using remote energy transfer.

The present invention may also be used for scoliosis correction that includes on-going adjustment, without a need for repeated surgical intervention or for fusion.

Figure 14:
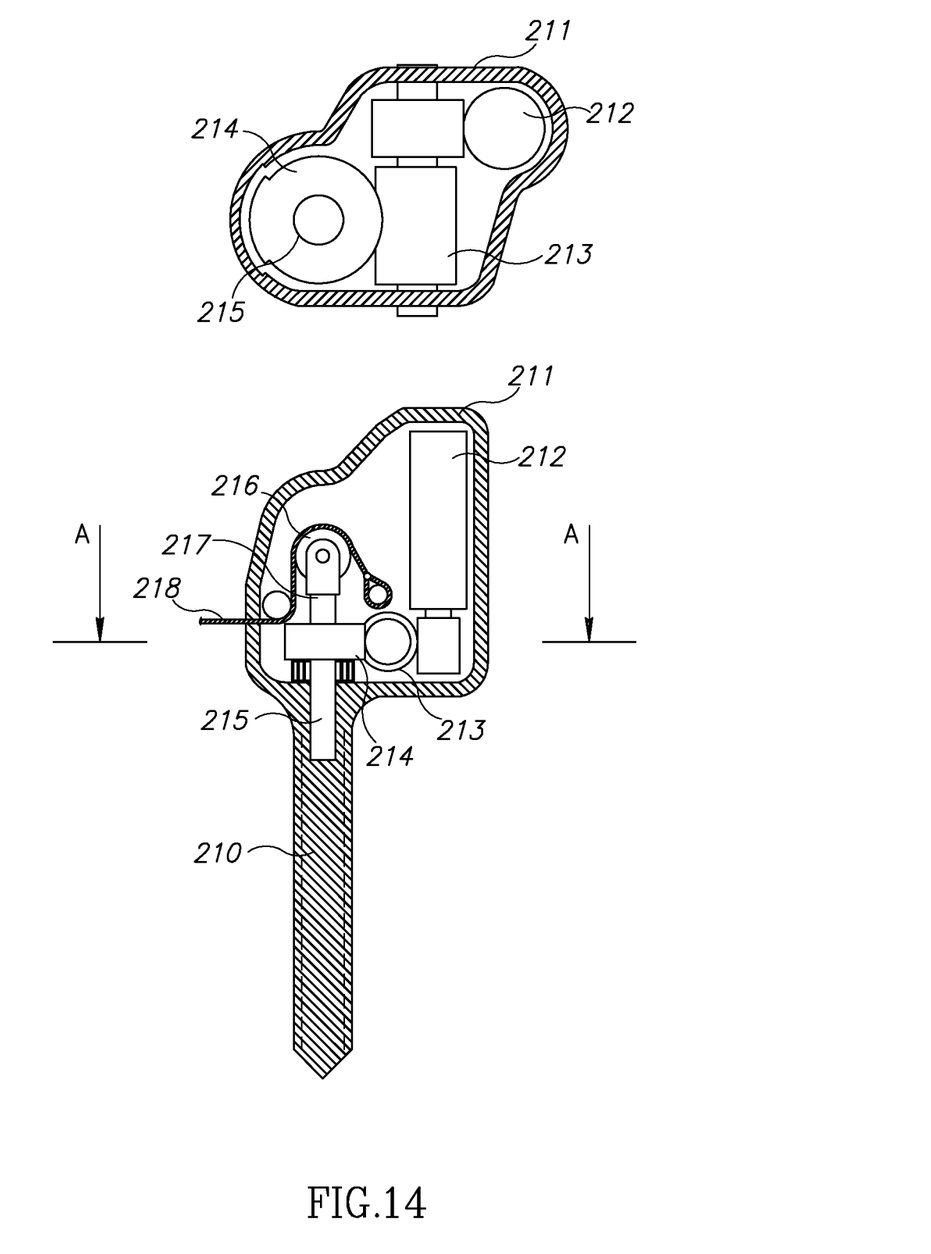
FIG. 14 is a simplified pictorial illustration of a spinal implant including a post-implantation variable dimension device, constructed and operative in accordance with another embodiment of the invention.

For example, reference is now made to FIG. 14, which illustrates a spinal implant including a post-implantation variable dimension device, constructed and operative in accordance with another embodiment of the invention.

The device includes a bone screw 210 that may be curved as part of, or rigidly attached to, a housing 211. A cable or wire 218 protrudes out of housing 211. The cable 218 is mounted over a roller 216. Roller 216 is connected to a screw 215 that can be moved linearly by rotating a gear 214 that meshes with screw 215. An electrical motor 212 powers a gear train 213 that controls the rotation of gear 214 and thus also the linear motion of screw 215 and the cable 218.

The design allows pulling or releasing cable 218 by operating the electrical motor 212 to different directions, at any given time after the implantation.

The embodiment of FIG. 14 can be inserted into the pedicles of the spinal vertebra or, alternatively, to the lateral side of the vertebra. Cable or wire 218 protruding from the side of the implant can be connected, using various different methods, to the adjacent implant or to another anchor, inserted into other vertebrae. When the cable or wire 218 is pulled by the abovementioned mechanism, the two vertebrae will be forced on to each other.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A spinal implant comprising:
   first spinal attachment member, having a top surface and an inner surface, for attaching to a first spinal portion;
   second spinal attachment member, having a bottom surface and an inner surface, for attaching to a second spinal portion; and
   a post-implantation variable dimension device disposed between said first and second spinal attachment members, which is operable after completing surgery in which said spinal implant was installed into a patient, to cause relative movement between said first and second spinal attachment members;
   wherein said post-implantation variable dimension device comprises threaded shafts, which do not have a common longitudinal axis, driven by a gear train activated by a remotely controlled motor, wherein said first and second spinal attachment members are each tapped with threaded through holes to accept said threaded shafts to allow said threaded shafts to move through said top surface of said first spinal attachment member and said bottom surface of said second spinal attachment member and to thereby move said first spinal attachment member with respect to said second spinal attachment member.

2. The spinal implant according to claim 1, further comprising a processor that is programmable to be activated at any desired time interval for any desired load and travel limits.

3. The spinal implant according to claim 1, wherein said post-implantation variable dimension device comprises circuitry for operating in a sleep mode.

4. The spinal implant according to claim 1, wherein said post-implantation variable dimension device is powered by a battery disposed in said spinal implant.

5. The spinal implant according to claim 4, wherein said battery is chargeable using remote energy transfer.

6. The spinal implant according to claim 1, wherein said first and second spinal attachment members are each tapped with threaded holes to accept said threaded shafts, and gear pulleys are connected to said threaded shafts and are driven by a gear, wherein rotation of said gear changes a distance between said first and second spinal attachment members.

7. The spinal implant according to claim 1, wherein some of said threaded shafts have left-handed threads and some of said threaded shafts have right-handed threads.

8. A spinal implant for causing distraction between a superior spinous process and an inferior spinous process in a body, the implant comprising:
   a first support plate, having a top surface and an inner surface, positioned inferiorly to the superior spinous process;
   a second support plate, having a bottom surface and an inner surface, positioned superiorly to the inferior spinous process; and
   a post-implantation variable dimension device disposed between said first and second support plates, which is operable after completing surgery in which said spinal implant was installed into a patient to cause relative movement between said first and second spinal attachment members, wherein said post-implantation variable dimension device comprises threaded shafts, which do not have a common longitudinal axis, and which are turned by a gear train activated by a remotely controlled motor, wherein rotation of said gear train causes said first support plate to push against the superior spinous process in a superior direction and said second support plate to push against the inferior spinous process in an inferior direction and changes a distance between said first and second support plates; and
   wherein said first and second support plates are each tapped with threaded through holes to accept said threaded shafts to allow said threaded shafts to move through said top surface of said first support plate and said bottom surface of said second support plate and to thereby move said first support plate with respect to said second support plate.

9. The spinal implant according to claim 8, wherein said first and second support plates are positioned between said threaded shafts.

10. The spinal implant according to claim 1, wherein said threaded shafts are encapsulated in said first and second attachment members.

* * * * *